(12) United States Patent
Meliniotis et al.

(10) Patent No.: US 10,953,165 B2
(45) Date of Patent: Mar. 23, 2021

(54) DRY POWDER INHALER

(71) Applicant: VECTURA DELIVERY DEVICES LIMITED, Wiltshire (GB)

(72) Inventors: Andreas Meliniotis, Cambridgeshire (GB); Liam McGuinness, Cambridgeshire (GB)

(73) Assignee: VECTURA DELIVERY DEVICES LIMITED, Wiltshire (GB)

( * ) Notice: Subject to any disclaimer, the term of this patent is extended or adjusted under 35 U.S.C. 154(b) by 404 days.

(21) Appl. No.: 15/745,965

(22) PCT Filed: Jul. 19, 2016

(86) PCT No.: PCT/EP2016/067208
§ 371 (c)(1),
(2) Date: Jan. 18, 2018

(87) PCT Pub. No.: WO2017/013130
PCT Pub. Date: Jan. 26, 2017

(65) Prior Publication Data
US 2018/0214647 A1     Aug. 2, 2018

(30) Foreign Application Priority Data
Jul. 20, 2015   (EP) ..................................... 15177556

(51) Int. Cl.
*A61M 15/00* (2006.01)
*A61M 11/02* (2006.01)
*A61M 15/08* (2006.01)

(52) U.S. Cl.
CPC .... *A61M 15/0055* (2014.02); *A61M 15/0021* (2014.02); *A61M 15/0026* (2014.02);
(Continued)

(58) Field of Classification Search
CPC .......... A61M 15/0051; A61M 15/0055; A61M 15/0056; A61M 15/0026; A61M 15/0036;
(Continued)

(56) References Cited

U.S. PATENT DOCUMENTS

2008/0163868 A1   6/2008   Pocock et al.
2010/0139654 A1*  6/2010   Thoemmes ....... A61M 15/0045
                                                    128/203.15
(Continued)

FOREIGN PATENT DOCUMENTS

CN         201131997 Y      10/2008
CN         101384289 A       3/2009
(Continued)

OTHER PUBLICATIONS

International Search Report from International Application No. PCT/EP2016/067208, dated Aug. 23, 2016.
(Continued)

*Primary Examiner* — Joseph D. Boecker
*Assistant Examiner* — Thomas W Greig
(74) *Attorney, Agent, or Firm* — Davidson, Davidson & Kappel, LLC

(57) ABSTRACT

A dry powder inhaler (10) having a chamber (26) divided into first and second blister compartments (28, 30) for storing unused and used portions (34, 36) of a blister strip (12) is provided. A moveable dividing wall (32) separates the first and second blister compartments. One or more arcuate supporting surfaces (38, 40, 42) are disposed in either the first and/or the second blister compartments and these surfaces support the used or unused blister strip during successive actuations of the inhaler. Use of the arcuate supporting surfaces facilities compact coils of unused and used portions of blister strip, thereby reducing the size of the chamber required for the inhaler.

13 Claims, 9 Drawing Sheets

(52) U.S. Cl.
CPC .... *A61M 15/0036* (2014.02); *A61M 15/0041* (2014.02); *A61M 15/0051* (2014.02); *A61M 15/0056* (2014.02); *A61M 11/02* (2013.01); *A61M 15/08* (2013.01); *A61M 2202/064* (2013.01)

(58) Field of Classification Search
CPC .. A61M 15/0041; A61M 5/00; A61M 5/0036; A61M 5/0041; A61M 5/0026; A61M 5/0051; A61M 5/0055; A61M 5/0056; A61M 5/08
See application file for complete search history.

(56) References Cited

U.S. PATENT DOCUMENTS

| | | | | |
|---|---|---|---|---|
| 2010/0288278 | A1* | 11/2010 | Pocock | A61M 15/0045 128/203.21 |
| 2011/0048419 | A1 | 3/2011 | Kirniak | |
| 2012/0132205 | A1* | 5/2012 | Meliniotis | A61M 15/0081 128/203.21 |
| 2014/0290653 | A1* | 10/2014 | Colomb | A61M 15/0026 128/203.15 |

FOREIGN PATENT DOCUMENTS

| | | | | |
|---|---|---|---|---|
| CN | 102056642 | A | 5/2011 | |
| GB | 2476490 | A | 6/2011 | |
| GB | 2502350 | A * | 11/2013 | ........ A61M 15/0041 |
| JP | 2008-161696 | | 7/2008 | |
| WO | WO2009007352 | A2 | 1/2009 | |
| WO | WO2012069854 | A2 | 5/2012 | |
| WO | WO2013175176 | A1 | 11/2013 | |
| WO | WO2015049611 | A1 | 4/2015 | |

OTHER PUBLICATIONS

Communication from the Chinese Patent Office in corresponding Chinese Patent Application No. 20168051517 20160719 dated Jan. 22, 2020.

Communication from the European Patent Office in corresponding European Patent Application No. 15177556.6 dated Dec. 1, 2015.

* cited by examiner

DRY POWDER INHALER

This application is a U.S. national phase application under 35 U.S.C. of § 371 of International Application No. PCT/EP2016/067208, filed Jul. 19, 2016, which claims priority of European Patent Application No. 15177556.6, filed Jul. 20, 2015, the disclosure of which is hereby incorporated by reference herein.

The present invention relates to an inhalation device for oral or nasal delivery of medicament in powdered form. More specifically, the invention relates to a dry powder inhaler in which powdered medicament is stored within a strip of blisters. The invention also relates to an inhaler containing a strip of blisters each having a puncturable lid and containing a dose of medicament for inhalation by a user of the device according to the invention.

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs, thereby avoiding the need for hypodermic injections.

It is common for dry powder formulations to be prepackaged in individual doses, usually in the form of capsules or blisters which each contain a single dose of the powder which has been accurately and consistently measured. A blister is generally cold formed from a ductile foil laminate or a plastics material and includes a lid which is permanently or peelably sealed around the periphery of the blister during manufacture and after the dose has been introduced into the blister.

A foil blister is preferred over capsules as each dose is protected from the ingress of water and penetration of gases such as oxygen in addition to being shielded from light and UV radiation, all of which can have a detrimental effect on the delivery characteristics of the inhaler if a dose becomes exposed to them. Therefore, a blister offers excellent environmental protection to each individual drug dose.

Inhalation devices that receive a coiled blister strip comprising a number of blisters each of which contain a pre-metered and individually packaged dose of the drug to be delivered are well known. Actuation of the device causes a mechanism to breach or rupture a blister, such as by puncturing it or peeling the lid off, so that when the patient inhales, air is drawn through the blister entraining the dose therein that is then carried out of the blister through the device and via the patient's airway down into the lungs. Pressurized air or gas or other propellants may also be used to carry the dose out of the blister. Alternatively, the mechanism that punctures or opens the blister may push or eject the dose out of the blister into a receptacle from which the dose may subsequently be inhaled.

It is advantageous for the inhaler to be capable of holding a number of doses to enable it to be used repeatedly over a period of time without the requirement to open and/or insert a blister into the device each time it is used. Therefore, many conventional devices include means for storing a number of blisters each containing an individual dose of medicament. When a dose is to be inhaled, an indexing mechanism moves a previously emptied blister away from the opening mechanism so that a fresh one, a target blister, is moved into a position ready to be opened for inhalation of its contents. An inhaler of this type is known from the Applicant's own international patent application which published as WO2005/037353 A1.

The device known from WO2005/037353 A1 has already been modified so as provide a fully integrated device, i.e. one in which the used blisters are retained within its housing so that a user never has to come into direct contact with the blister strip.

In one modified embodiment, known from the Applicant's own previous application that has now been published as WO2009/007352 A1, there is provided a flexible and resilient spiral element mounted within the housing of the device into which the used portion of the blister strip is directed so that, as the strip is gradually used up, the spiral expands as more and more of the strip is fed or pushed into it between its coils.

Like the present invention, the device in WO2009/007352 A1 has a dividing wall to separate the interior of the housing into used and unused blister compartments. The dividing wall is rigid and slideably mounted so that the size of the unused and used blister compartments changes relative to each other as the number of blisters that are used increases and the number of unused blisters decreases. A moveable wall is also known from US 2010/0288278 (Valois S.A.S.).

WO09/007352 A1 also describes an embodiment in which used blisters are crushed between the blister strip drive or indexing wheel and the inner surface of the casing of the device, which is also a feature of the inhaler of the present invention. As crushing takes place, i.e. as the used strip passes around the blister strip drive member, a curl or curved form is imparted to the strip which helps it to coil up within the used blister compartment.

A full operation of the inhaler according to the present invention is described in WO2012/069854 A1. The indexing mechanism is specifically described in WO2009/092652 A1.

The disclosures of WO2005/037353 A1, WO09/007352 A1, WO2009/092652 A1 and WO2012/069854 A1 are all incorporated herein by reference.

The present invention seeks to provide an inhalation device that retains a used blister strip within the housing of the device, whilst optimising the internal configuration in order to enhance the compactness of the device.

According to a first aspect of the invention, there is provided an inhaler comprising
- a housing,
- a mouthpiece,
- a blister strip having a plurality of blisters, each blister containing, at least initially, a dose of medicament for inhalation by a user via the mouthpiece,
- a blister opening assembly for facilitating withdrawal of medicament from a target blister of the blister strip,
- an actuator mechanism operable to sequentially move each blister into alignment with the blister opening assembly so as to become said target blister,
- the housing comprising a first blister compartment for storing an unopened portion of the blister strip as a first coil, a second blister compartment for receiving an opened portion of the blister strip and coiling it into a second coil, and a movable dividing wall separating the first and second blister compartments,
- the movable dividing wall being displaced progressively during successive actuations of the inhaler, thereby causing the volume of the first blister compartment to decrease progressively and the volume of the second blister compartment to increase progressively,
- the inhaler further comprising an arcuate supporting surface within the housing for supporting at least a portion of the first or second coils.

Optionally, a radius of the arcuate supporting surface matches the radius of the first coil, at a stage in the life of the inhaler, when the diameter of the first coil is at a maximum.

Optionally, a radius of the arcuate supporting surface matches the radius of the first coil, at a stage in the life of the inhaler, when the sum diameter of the first and second coils is at a maximum.

Optionally, a radius of the arcuate supporting surface matches the radius of the second coil, at a stage in the life of the inhaler, when the diameter of the first coil is at or near a maximum.

The arcuate supporting surface may be disposed in, or form part of, the first blister compartment.

The arcuate supporting surface may be disposed in, or form part of, the second blister compartment.

Preferably, the arcuate supporting surface extends from an internal surface of the housing. Alternatively, the arcuate supporting surface may extend from an internal wall within the housing.

Preferably, the arcuate supporting surface has a length equivalent to an arc of the first coil of at least 30 degrees when the diameter of the first coil is at a maximum.

Preferably, the position of the arcuate supporting surface relative to the housing is fixed such that it is immoveable.

The first coil may be disposed intermediate the arcuate supporting surface and the moveable dividing wall. Alternatively, the second coil may be disposed intermediate the arcuate supporting surface and the moveable dividing wall.

Preferably, the inhaler further comprises a blister strip guide rib for controlling the direction of the used blister strip as it enters the second blister compartment, the used blister strip passing between the guide rib and an internal surface of the housing during successive actuations of the inhaler. Ideally, the blister strip has a height a and the guide rib is spaced apart from the internal surface of the housing by distance b, wherein distance b is less than height a.

Optionally, the inhaler further comprises a blister crushing member for at least partially squashing the blisters after they have been opened.

Preferably, the arcuate supporting surface has a thickness of up to 1 mm. Preferably, the arcuate supporting surface is spaced apart from the moveable dividing wall.

Preferably, the arcuate supporting surface is inflexible or rigid.

Optionally, the movable dividing wall may be configured to facilitate the formation of the second coil as the used portion of the blister strip enters the second blister compartment.

Preferably, the blister strip carries between 30 and 60 blisters.

Preferably, each blister has a dose payload of up to 100 mg, preferably up to 50 mg, and more preferably between 10 and 25 mg.

According to a second aspect of the invention there is provided an inhaler, comprising
  a housing,
  a mouthpiece,
  a blister strip having a plurality of blisters, each blister containing, at least initially, a dose of medicament for inhalation by a user via the mouthpiece,
  a blister opening assembly for facilitating withdrawal of medicament from a target blister of the blister strip,
  an actuator mechanism operable to sequentially move each blister into alignment with the blister opening assembly so as to become said target blister,
  the housing comprising a first blister compartment for storing an unopened portion of the blister strip as a first coil, a second blister compartment for receiving an opened portion of the blister strip and coiling it into a second coil, and a movable dividing wall separating the first and second blister compartments,
  the movable dividing wall being displaced progressively during successive actuations of the inhaler, thereby causing the volume of the first blister compartment to decrease progressively and the volume of the second blister compartment to increase progressively,
  the inhaler further comprising an arcuate supporting surface within the housing for supporting at least a portion of the first coil,
  characterised in that a radius of the arcuate supporting surface matches the radius of the first coil, at a stage in the life of the inhaler, when the diameter of the first coil is at a maximum.

According to a third aspect of the invention, there is provided an inhaler, comprising
  a housing,
  a mouthpiece,
  a blister strip having a plurality of blisters, each blister containing, at least initially, a dose of medicament for inhalation by a user via the mouthpiece,
  a blister opening assembly for facilitating withdrawal of medicament from a target blister of the blister strip,
  an actuator mechanism operable to sequentially move each blister into alignment with the blister opening assembly so as to become said target blister,
  the housing comprising a first blister compartment for storing an unopened portion of the blister strip as a first coil, a second blister compartment for receiving an opened portion of the blister strip and coiling it into a second coil, and a movable dividing wall separating the first and second blister compartments,
  the movable dividing wall being displaced progressively during successive actuations of the inhaler, thereby causing the volume of the first blister compartment to decrease progressively and the volume of the second blister compartment to increase progressively,
  the inhaler further comprising an arcuate supporting surface within the housing for supporting at least a portion of the first coil,
  characterised in that a radius of the arcuate supporting surface matches the radius of the first coil, at a stage in the life of the inhaler, when the sum diameter of the first and second coils is at a maximum.

According to a fourth aspect of the invention, there is provided an inhaler, comprising
  a housing,
  a mouthpiece,
  a blister strip having a plurality of blisters, each blister containing, at least initially, a dose of medicament for inhalation by a user via the mouthpiece,
  a blister opening assembly for facilitating withdrawal of medicament from a target blister of the blister strip,
  an actuator mechanism operable to sequentially move each blister into alignment with the blister opening assembly so as to become said target blister,
  the housing comprising a first blister compartment for storing an unopened portion of the blister strip as a first coil, a second blister compartment for receiving an opened portion of the blister strip and coiling it into a second coil, and a movable dividing wall separating the first and second blister compartments, the movable dividing wall being displaced progressively during successive actuations of the inhaler, thereby causing the volume of the first blister compartment to decrease progressively and the volume of the second blister compartment to increase progressively, the inhaler further comprising an arcuate supporting surface within the housing for supporting at least a portion of the second coil, characterised in that a radius of the arcuate supporting surface matches the radius of the second coil, at a stage in the life of the inhaler, when the diameter of the first coil is at or near a maximum.

This coincides with a stage in the life of the inhaler when the diameter of the second coil is at a minimum.

According to a fifth aspect of the invention, there is provided an inhaler, comprising a housing, a mouthpiece extending from or mounted to the housing, a blister strip having a plurality of blisters, each blister containing, at least initially, a dose of medicament for inhalation by a user via the mouthpiece, a blister opening assembly for facilitating withdrawal of medicament from a target blister of the blister strip, an actuator mechanism operable to sequentially move each blister into alignment with the blister opening assembly so as to become said target blister, the housing comprising a first blister compartment for storing an unopened portion of the blister strip as a first coil, a second blister compartment for receiving an opened portion of the blister strip and coiling it into a second coil, and a movable dividing wall separating the first and second blister compartments, the movable dividing wall being displaced progressively during successive actuations of the inhaler, thereby causing the volume of the first blister compartment to decrease progressively and the volume of the second blister compartment to increase progressively, the inhaler further comprising an arcuate supporting surface in the first blister compartment for supporting at least a portion of the first coil, a second said arcuate supporting surface in the first blister compartment for supporting a further portion of the first coil and a third said arcuate supporting surface in the second blister compartment for supporting a portion of the second coil.

Preferably, the inhaler further comprises a blister strip guide rib for controlling the direction of the used blister strip as it enters the second blister compartment, the used blister strip passing between the guide rib and an internal surface of the housing during successive actuations of the inhaler. Ideally, the blister strip has a height a and the guide rib is spaced apart from the internal surface of the housing by distance b, wherein distance b is less than height a.

Embodiments of the invention will now be described, by way of example only, with reference to FIGS. 1 to 9 of the accompanying drawings, in which.

Figure 1:
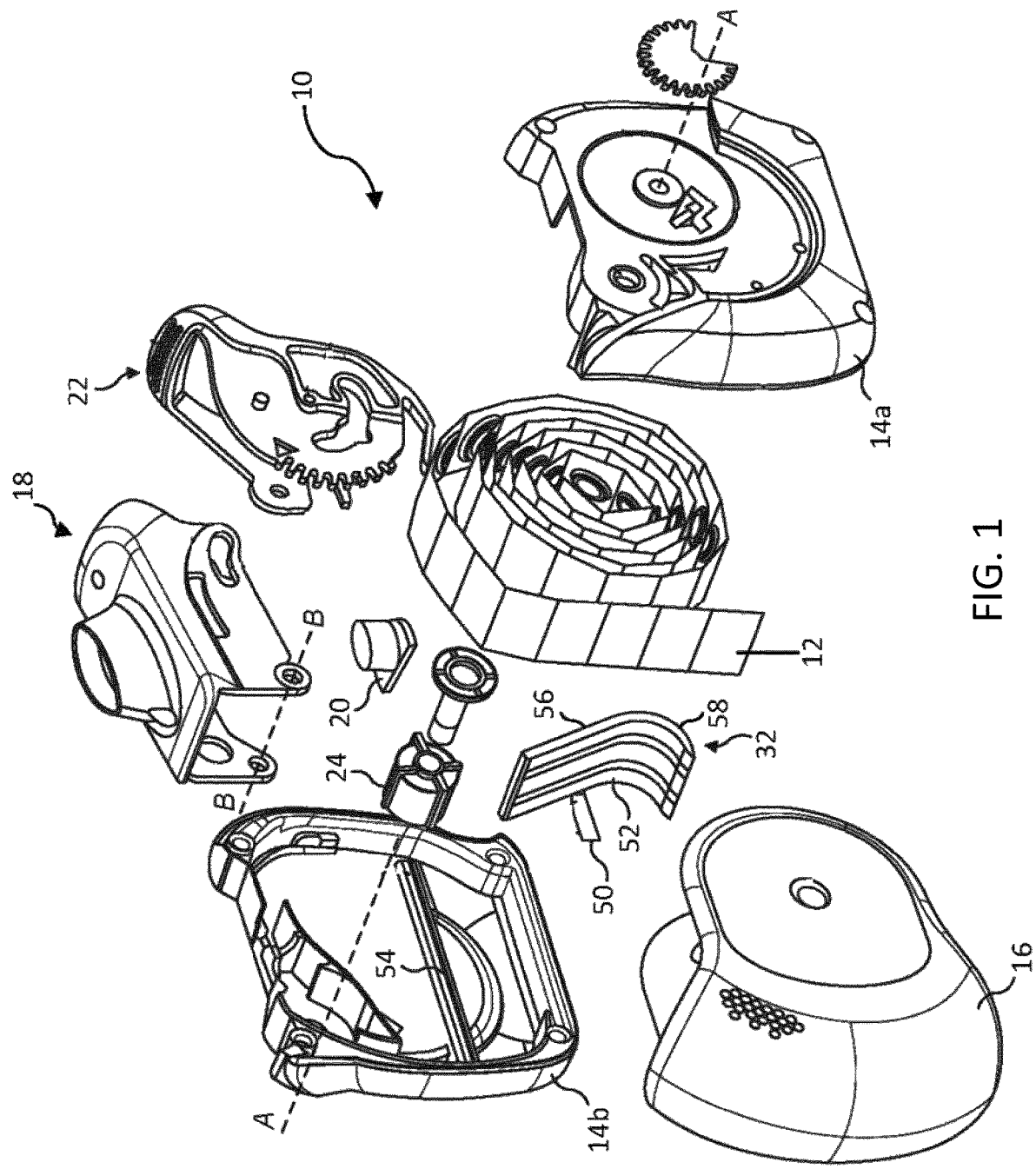
FIG. 1 is an exploded perspective view showing the individual components of an inhaler according to the invention.

Referring to FIGS. 1 and 2 of the accompanying drawings, there is shown a dry powder inhaler 10 for dispensing powdered medicament from a blister strip 12. The inhaler 10 comprises a housing 14 formed from two shell portions 14a, 14b a cap 16 pivotally mounted to the housing 14 for rotation about a first axis of rotation A, a mouthpiece 18 pivotally mounted to the housing 14 about a second axis of rotation B, a blister piercing member 20 depending from the mouthpiece 18 for piercing the blister strip 12, an indexing system for advancing the blister strip 12 past the blister piercing member 20 and an actuating lever 22 operable to cause both indexing and piercing of the blister strip 12.

Figure 2A:
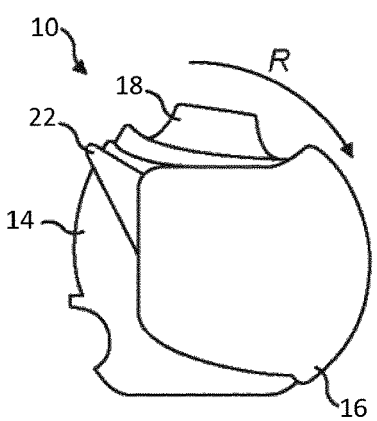
FIGS. 2a to 2e is a sequence of drawings to show the general function and operation of the inhaler.

The cap 16 is moveable, from a closed position in which the cap 16 covers and protects the mouthpiece 18, to a fully open position, and in a direction indicated by arrow "R" in FIG. 2(a), in which the mouthpiece 18 is exposed to enable a user to inhale a dose of medicament through the mouthpiece 18 from the blister strip 12.

The cap 16 is rotated into its fully open position in the direction of arrow "R". The actuating lever 22 is revealed as soon as the cap 16 is rotated out of its closed position. The user then applies pressure to the actuating lever 22, so that it rotates in the direction indicated by arrow "S" in FIG. 2(b).

Figure 2B:
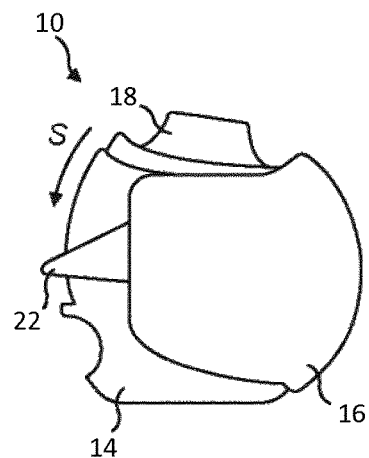

During initial rotation of the actuating lever 22 through a first portion of its stroke into the position as it is shown in FIG. 2(b), the blister strip 12 is indexed so as to move an unused blister into alignment with the blister piercing member 20.

Figure 2C:
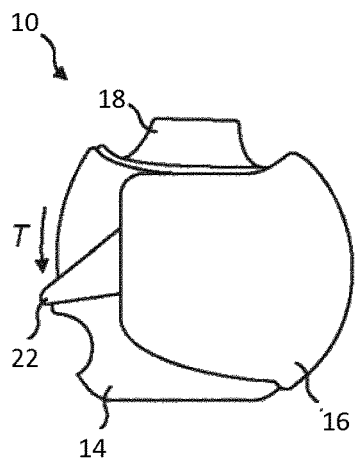

When the actuating lever 22 is rotated through a second portion of its stroke beyond the position shown in FIG. 2(b) and after having completed the first portion of its stroke, in the direction of arrow "T" in FIG. 2(c), the blister strip 12 remains stationary but the mouthpiece 18 is now pivoted so that the blister piercing member 20 pierces the lid of the previously aligned blister.

Figure 2D:
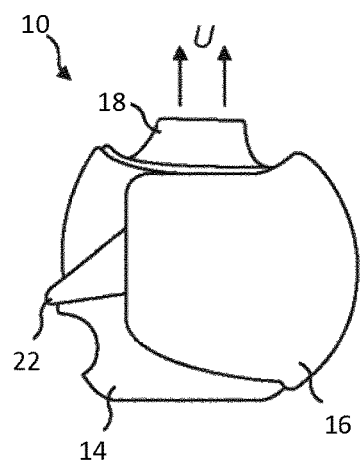

Once the actuating lever 22 is in the position shown in FIG. 2(c), the user now inhales through the mouthpiece 18, as shown by arrows indicated by "U" in FIG. 2(d).

Figure 2E:
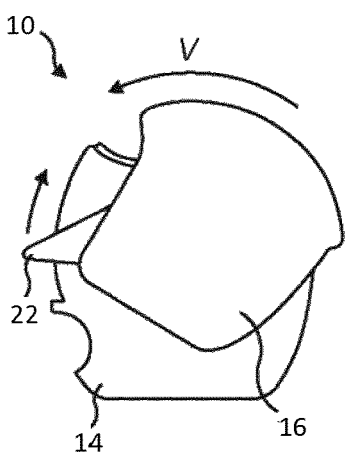

After inhalation, the user rotates the cap 16 in the opposite direction, i.e. in the direction indicated by "V" in FIG. 2(e). During this movement, the cap 16 engages with the actuating lever 22 so that the actuating lever 22 also returns to its initial position as shown in FIG. 2(a), the blister strip remaining stationary during this return movement of the actuating lever 22.

It should be noted that the cap 16 is 'passive' in the sense that it can be opened and closed freely without performing the function of indexing of the blister strip 12 or causing a blister piercing member 20 depending from the mouthpiece 18 to pierce the lid of an aligned blister. However, although the cap 16 is passive, it does perform the function of re-setting the actuating lever back to its original position in the event that the actuating lever 22 is depressed prior to closing the cap 16.

The cap 16 and actuating lever 22 are configured so that, when the cap 16 is in its closed position and the actuating lever 22 has returned to its initial position, the cap 16 overlies the actuating lever 22 which is pressed by a user to operate the device. This prevents a user from attempting to operate the device by rotating the actuating lever 22 prior to opening the cap 16.

As previously mentioned, the inhaler 10 has an indexing mechanism that has previously been described in WO2009/092652 A1 and a thus further detailed description will be omitted here.

The indexing mechanism comprises a blister strip drive member or indexing wheel 24, around which the used blister strip travels, and which drives the blister strip 12 onwards. The indexing wheel 24 may also be used to squeeze the used blister cavities as they pass around it, thereby at least partially crushing them. This is achieved by enlarging the axle or hub of the indexing wheel 24 so that the distance between the hub and the casing or wall of the inhaler 10, or a component fixed to the casing, is less than the maximum height of a blister cavity. As the blister cavities are entrained between spokes of the indexing wheel 24, onward rotation of the indexing wheel 24 causes the cavities to be at least partially squashed or sandwiched between the enlarged hub of the indexing wheel 24 and the casing of the inhaler 10. The advantage of at least partially crushing the empty blister cavities is that they then take up less space when coiled within the used blister compartment of the device as the coiled strip has a smaller radius. Furthermore, a natural curvature is imparted to the strip, both as a result of being fed around the indexing wheel 24 and also as a result of the crushing of the blister cavities. This encourages the used portion of the blister strip 12 to coil more readily. It is also apparent that, when the blister cavities have been crushed, the cavity is more resilient to denting at the point at which the spoke of the indexing wheel 24 contacts the strip, i.e. at the root where the blister cavity meets the remainder of the blister strip 12. Therefore, a more positive and precise drive of the blister strip 12 is achieved when the blisters have been crushed.

Within the housing 14, a chamber 26 is separated into first and second compartments 28, 30 by a rigid dividing wall 32. The unused portion of blister strip 12 is stored within the first blister compartment 28 as a first coil 34 and the used portion of blister strip 12 is received into the second blister compartment 30 to form a second coil 36. The dividing wall 32 is slideably mounted within the chamber 26 so that, as more of the blisters are used, the force of the used coil 36 of blisters in the second blister compartment 30 presses against the dividing wall 32 and pushes it so as to enlarge the space for the used blisters and reduce the space previously occupied by the unused blisters.

It is here where the invention lies. The configuration of the interior of the housing 14 has been optimised to minimise the space required for the first and second blister compartments 28, 30, thereby reducing the overall size of the inhaler 10.

The inhaler 10 comprises three arcuate supporting surfaces 38, 40, 42 within the housing 14 for supporting at least a portion of the first coil 34, of the second coil 36, or both the first and second coils 34, 36 during successive actuations of the inhaler 10. In this embodiment, three distinct arcuate supporting surfaces 38, 40, 42 are provided, but any one or two combinations of the arcuate supporting surfaces 38, 40, 42 could feasibly be used. It is only when all three arcuate supporting surfaces 38, 40, 42 are used that the configuration is optimised. With only one or two arcuate supporting surfaces 38, 40, 42, the configuration is improved so that less space is required for the unused and used portions of blister strip 12, but it is not an optimum configuration, which is preferable.

Figure 3:
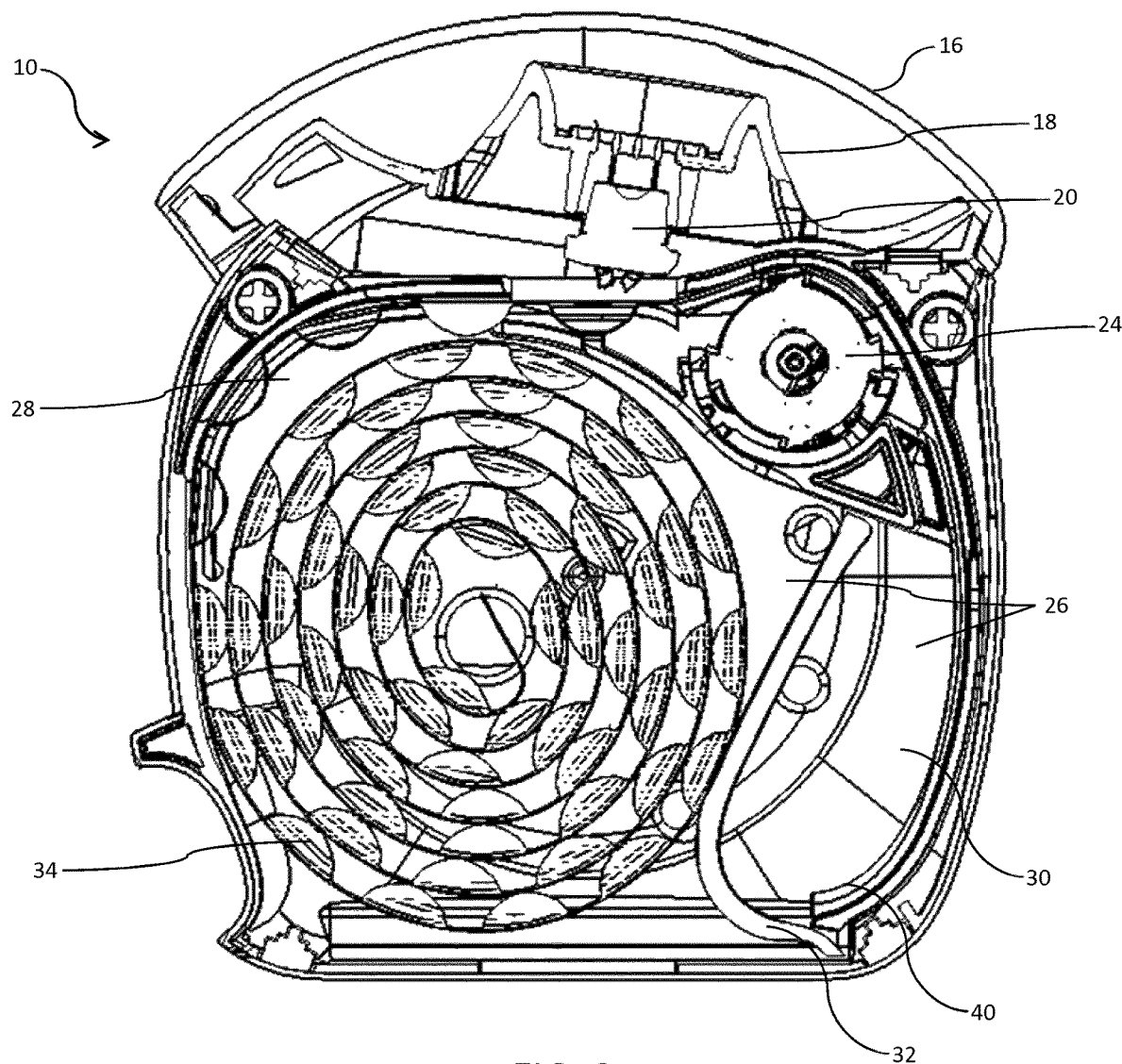
FIG. 3 is a cross-sectional side view of the inhaler, showing in particular a coiled portion of unused blister strip in a first blister compartment of the inhaler.

FIG. 3 shows the coil 34 of unused blister strip 12 after one or two actuations have taken place but before the second coil 36 has begun to form in the second blister compartment 30. The diameter of the first coil 34 is just less than its maximum.

Figure 4:
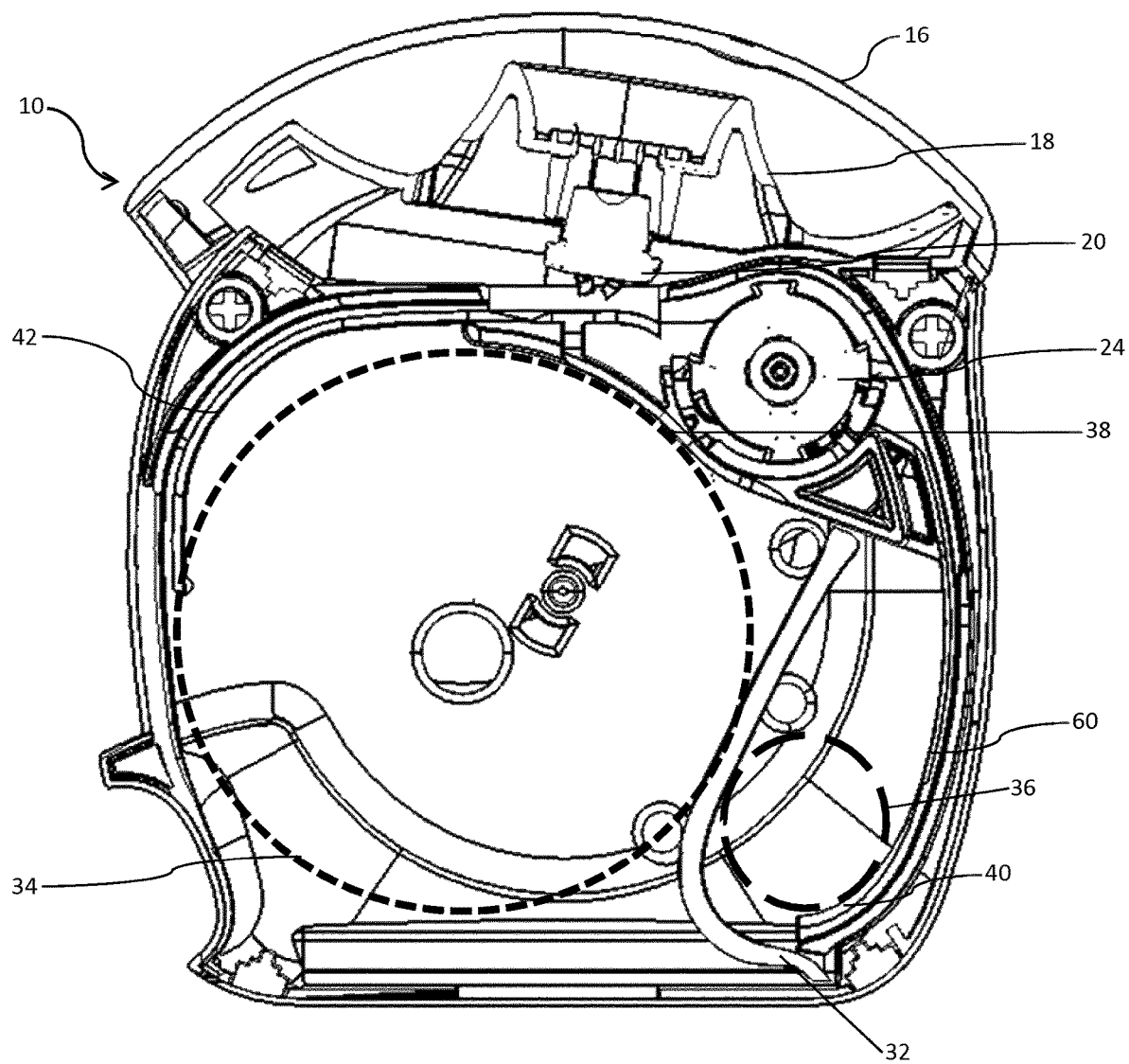
FIG. 4 is the cross-sectional side view of the inhaler of FIG. 3 but with the coiled blister strip removed for clarity, at the stage in the life of the inhaler when a diameter of the coiled portion of unused blister strip is at a maximum.

FIG. 4 indicates the coil 34 of unused blister strip 12 at or near its maximum diameter but with enough used blister strip in the second blister compartment 30 to form the second coil 36. In FIG. 4, a first arcuate supporting surface 38 is seen to support the theoretical outermost spiral of the first coil 34. The first arcuate supporting surface 38 forms part of the first blister compartment 28. The first arcuate supporting surface 38 extends from an internal wall of the inhaler 10, proximate to the indexing wheel 24.

In this position, the first arcuate supporting surface 38 supports the first coil 34 in a substantially central position within the inhaler 10, urging the moveable dividing wall 32 to the right hand side of the inhaler 10 as viewed in FIG. 4. The first arcuate supporting surface 38 has a length equivalent to an arc of the first coil 34 of at least 30 degrees when the diameter of the first coil 34 is at a maximum. This length of arcuate supporting surface provides sufficient support for the first coil 34 to hold it in place initially but without unnecessarily increasing the complexity of the design of the inhaler 10.

A second arcuate supporting surface 40 supports the second coil 36. The second arcuate supporting surface 40 forms part of the second blister compartment 30. The second arcuate supporting surface 40 is situated in the vicinity of the exit region of the indexing wheel 24. The length of the second arcuate supporting surface 40 is equivalent to an arc of the second coil 36 of at least 30 degrees when the diameter of the first coil 34 is at a maximum.

Thus, the configuration of the first and second blister compartments 28, 30 is specific to the stage in the life of the inhaler 10 when the diameter of the first coil 34 is at or near a maximum. It is also at this time, that the diameter of the second coil 36 is at a minimum. At this stage, the radius of the first arcuate supporting surface 38 matches the radius of the first coil 34. Also, the radius of the second arcuate supporting surface 40 matches the radius of the second coil 36.

Figure 5:
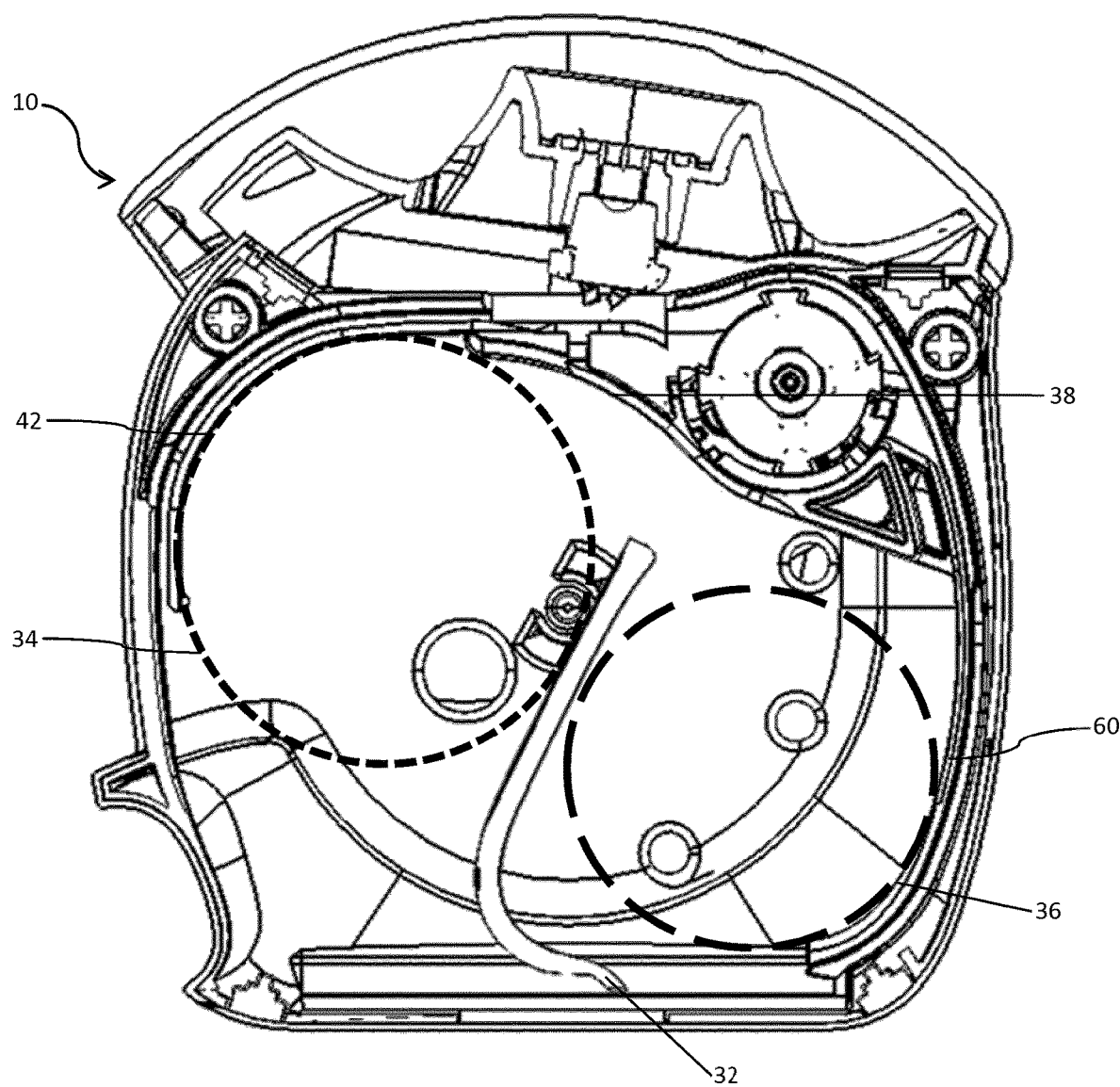
FIG. 5 is the cross-sectional side view of the inhaler of FIG. 3 again with the coiled blister strip removed, at the stage in the life of the inhaler when the sum diameter of the coiled portion of unused blister strip and a coiled portion of used blister strip is at a maximum.

Turning now to FIG. 5, a third arcuate supporting surface 42 extends inwardly from an internal surface of the inhaler 10. The third arcuate supporting surface 42 forms part of the first blister compartment 28. The third arcuate supporting surface 42 is situated in the vicinity of the entry region of the indexing wheel 24. Again, the length of the third arcuate supporting surface 42 is equivalent to an arc of the first coil 34 of at least 30 degrees when the diameter of the first coil 34 is at a maximum.

In FIG. 5, the configuration of the first and second compartments 28, 30 is specific to the stage in the life of the inhaler 10 when the combined diameter of the first and second coils 34, 36 is at a maximum. At this stage, the radius of the third arcuate supporting surface 42 matches the radius of the first coil 34.

Figure 6:
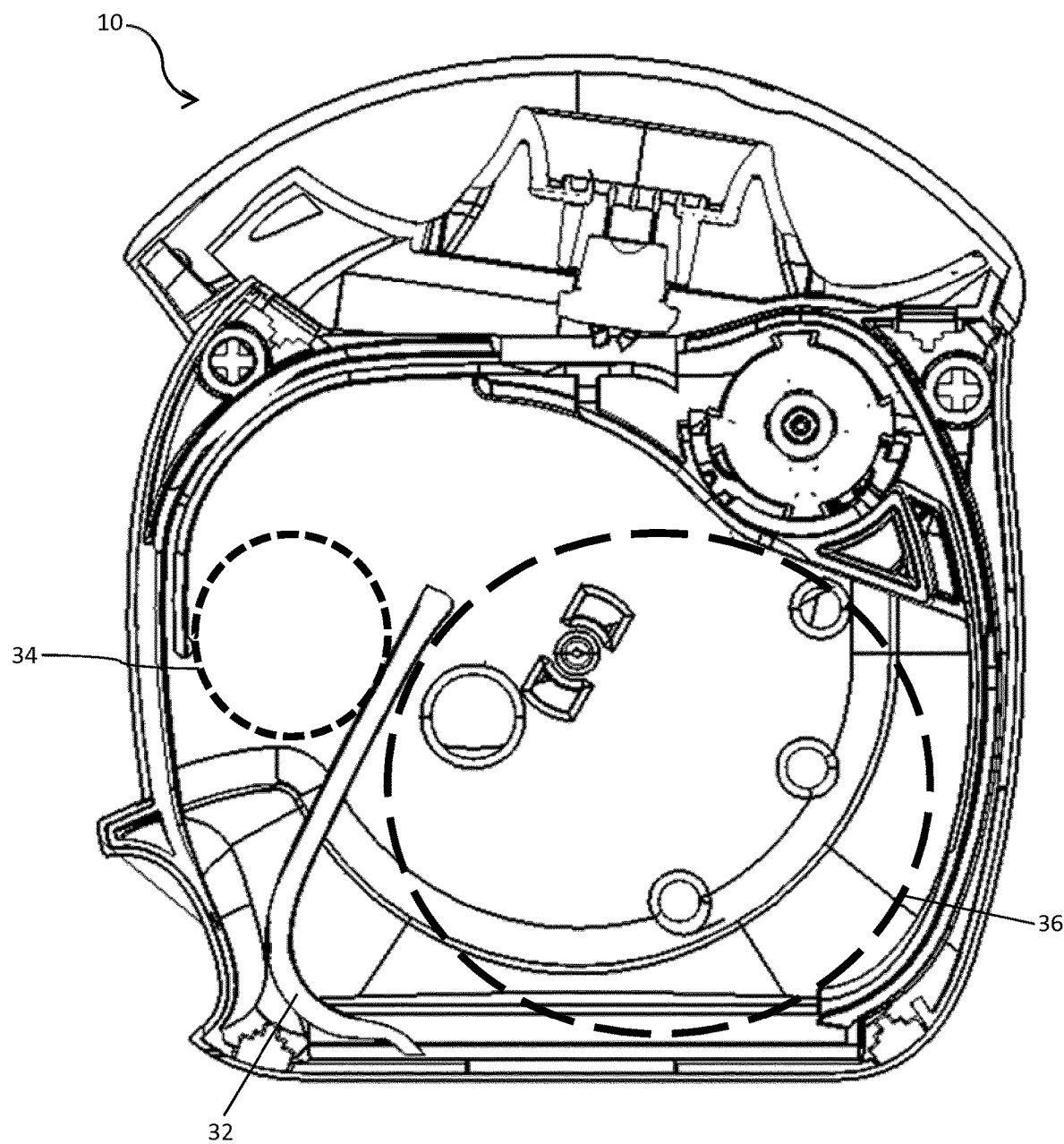
FIG. 6 is the cross-sectional side view of the inhaler of FIG. 3 yet again with the coiled blister strip removed, at the stage in the life of the inhaler when the diameter of the coiled portion of used blister strip is at a maximum.

In FIG. 6, all or almost all of the doses from the blister strip 12 have been dispensed from the inhaler 10. The configuration of the first and second blister compartments 28, 30 is specific to the stage in the life of the inhaler 10 when the diameter of the second coil 36 is at a maximum. This coincides with same stage as when the diameter of the first coil 34 is at or near a minimum.

Figure 7:
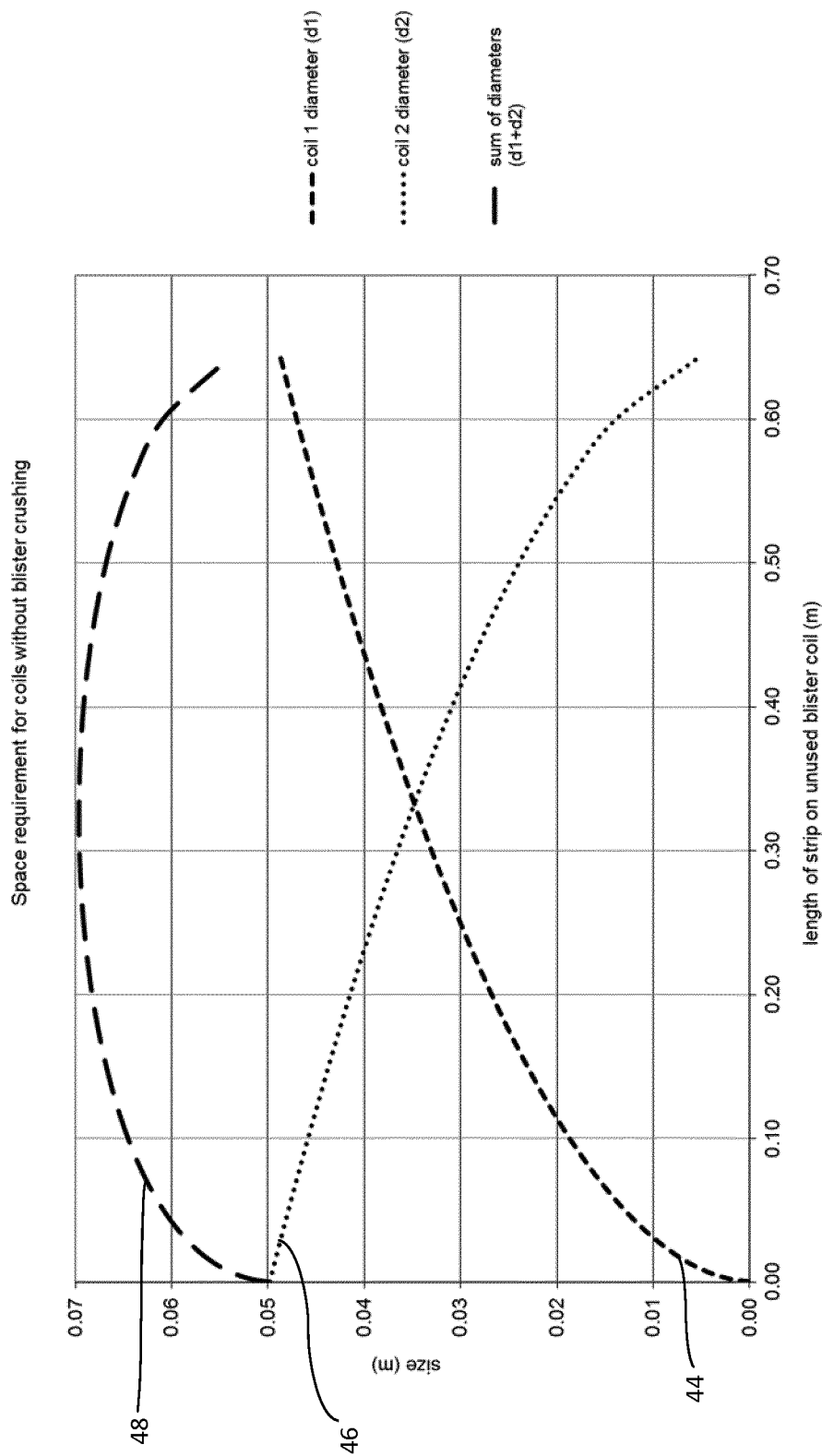
FIG. 7 is a graph showing the space requirements within the inhaler for the unused and used blister strip throughout the life of the inhaler, without blister crushing.

With reference to FIG. 7, the diameter of the first coil is indicated at curve 44, the diameter of the second coil at curve 46, and the sum of these two diameters, i.e. the sum diameter of the first and second coils is indicated at curve 48.

At the beginning of the life of the inhaler 10 when few or no doses have been dispensed, and also up to substantially mid-way through the life of the inhaler, it is very important for the space within the first and second blister compartments 28, 30 to be tightly controlled or allocated so as to minimise the internal volume required subsequently for the first and second coils 34, 36. If this did not happen, the curve 48 indicating the sum diameter of the first and second coils 34, 36 would shift upwardly and would begin at a much higher point on the graph. Consequently, the space required for the first and second coils 34, 36 when their combined diameters are at a maximum, i.e. the peak of the sum of diameters curve 48 occurring approximately mid-way through the life of the inhaler 10, would be higher. In brief, it is imperative that the combined diameter of the first and second coils is as small as possible at the start of the useful life of the inhaler.

At or towards the end of the life of the inhaler 10, the role of the arcuate supporting surfaces 38, 40, 42 becomes increasingly insignificant because there is less need now for the used blister strip to be coiled up tightly. In practice, the second coil 36 simply expands to fill most, if not all, of the space available within the second blister compartment 30.

Figure 8:
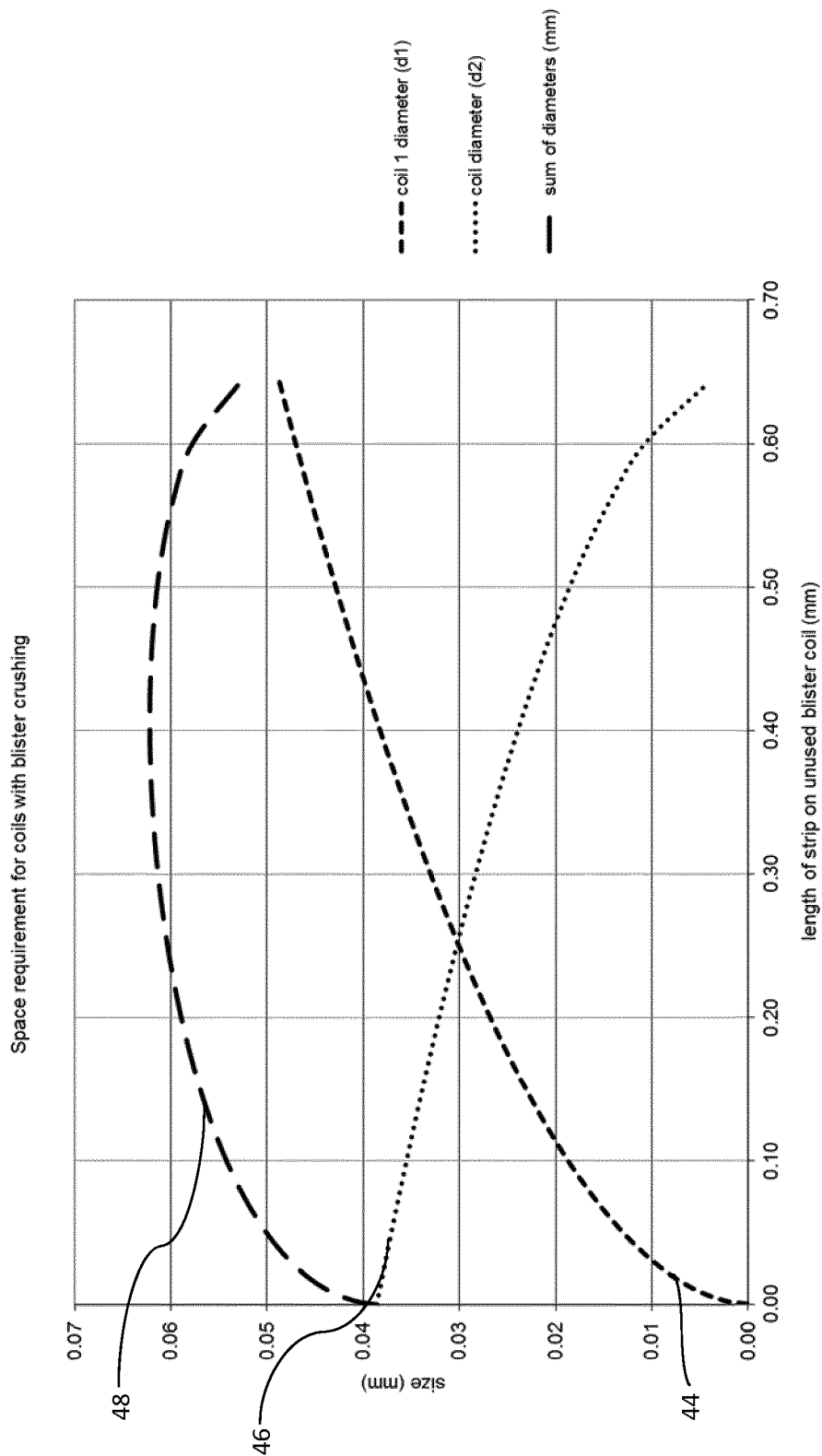
FIG. 8 is a graph similar to that in FIG. 8, but with blister crushing incorporated into the inhaler, demonstrating the effect of blister crushing on the space requirements within the inhaler.

When blister crushing is incorporated into the inhaler 10, as explained earlier, this reduces the sum diameter of the first and second coils 34, 36 generally throughout the life of the inhaler 10, as indicated in FIG. 8. In particular, the space required for the first and second coils 34, 36 when the combined diameter of the first and second coils 34, 36 is at a peak, is reduced compared to when no blister crushing is used.

Blister crushing does not affect the diameter of the first coil 34 since blister crushing takes place after blister piercing and dose inhalation has occurred. It does affect the diameter of the coiling used blister strip, and facilitates a tighter second coil 36. Therefore, the sum diameter of the first and second coils 34, 36 is less than when no blister crushing occurs.

It is clear from both FIGS. 7 and 8 that it is important to constrain the first and second coils 34, 36 as much as possible in the early stages of the life of the inhaler 10 in order to minimise the sum diameter of the first and second coils 34, 36. This, in turn, minimises the amount of space required when the sum diameter of the first and second coils 34, 36 is at its peak (or maximum). This is achieved by employing one or more the arcuate supporting surfaces 38, 40, 42 described above.

None of the aforementioned arcuate supporting surfaces 38, 40, 42 form part of the moveable dividing wall 32. For a period of time, the first arcuate supporting surface 38 is near to the moveable dividing wall 32, as the moveable dividing wall 32 travels across the breadth of the inhaler 10 from right to left as viewed when looking at FIGS. 4, 5 and 6. The second arcuate supporting surface 40 is separated from the moveable dividing wall 32 by the second coil 36. The third arcuate supporting surface 42 is separated from the moveable dividing wall 32 by the first coil 34.

In this embodiment of the invention, the moveable dividing wall 32 comprises an elongate foot 50 which is attached to and integrally formed with a baffle 52 that divides the chamber 26 within the inhaler 10 into the first and second blister compartments 28, 30. An approximate central region of the foot 50 is attached to the baffle 52 so that it extends in opposite directions on either side of the baffle 52. The foot 50 is slideably received in a recess 54 formed in a wall of the housing 14 and is wider at its ends than in its centre where it joins the baffle 52 so that contact with the walls of the recess 50 is primarily made with the wider ends of the foot 50.

The baffle 52 itself is generally 'J' shaped, with a linear body portion 56 and an arcuate tail portion 58 extending from a lower end of the linear body portion 56. The arcuate tail portion 58 is curved to encourage the incoming used blister strip within the second compartment 30 to curl tightly into the second coil 36. The smaller the radius of the arcuate tail portion 58, the tighter the second coil 36 becomes. The advantage of this is that the resulting second coil 36 is smaller when at its greatest radius than it would be otherwise.

Figure 9:
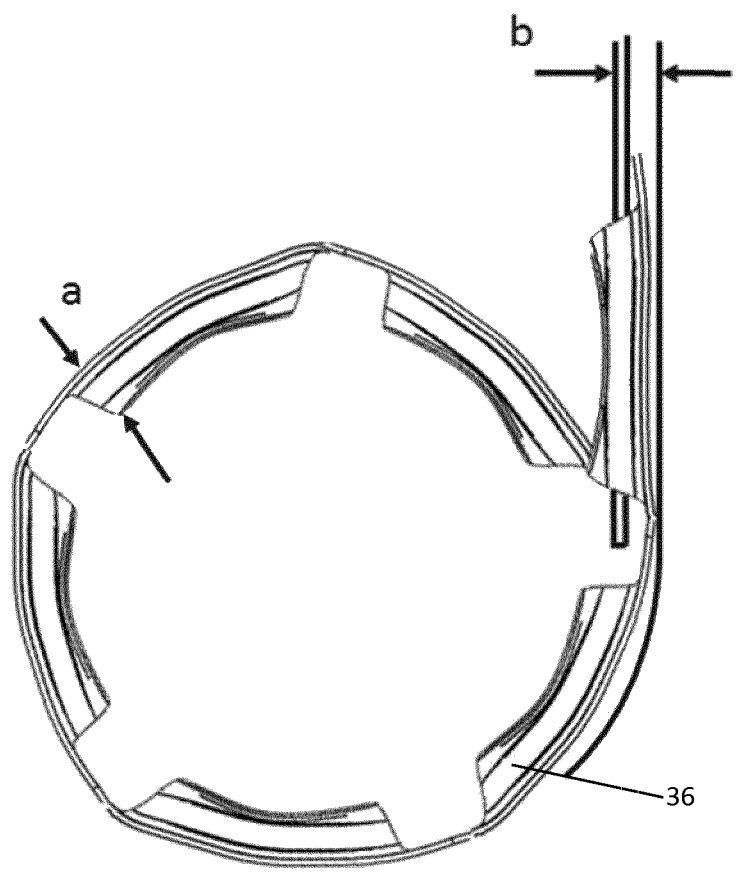
FIG. 9 is a schematic close-up view of the used blister strip entering into a second blister compartment and coiling back onto itself, to form an additional coil.

Turning now to FIG. 9, a blister strip guide rib 60 is positioned in the second blister compartment 30. The blister strip guide rib 60 controls the direction of the used blister strip as it enters the second blister compartment 30. A gap or channel exists between the blister strip guide rib 60 and the housing 14 to allow the used blister strip to pass therethrough during successive actuations of the inhaler 10. The size of the gap is important. If the blister strip 12 has a height a and the blister strip guide rib 60 is spaced apart from an internal surface of the housing 14 by a distance b, distance b must be less than height a.

The thickness of the blister strip guide rib 60 is critical. Too thin and the blister strip guide rib 60 is problematic during manufacturing. Too thick and the used blister strip will not coil tightly; instead the used blister strip will form an elongate (as opposed to rounded) loop that pushes away from the blister strip guide rib 60 towards the centre of the chamber 26, before eventually beginning to coil. The resulting diameter of the second coil 36 would therefore be a lot greater than it would be otherwise, thereby increasing the combined diameter of the first and second coils 34, 36, and consequently increasing the internal volume required for the used and unused blister strip 12. When the thickness of the rib is at an optimum value, as the used blister strip begins to coil, it will coil back on itself, and engage the incoming used blister strip. The force acting on the incoming blister strip to move it forward is consequently augmented by the force acting on the free end of the blister strip 12. The inventors have found the optimum thickness of the blister strip guide rib 60 to be up to 1 mm.

In terms of impact on the overall internal volume required, the blister strip guide rib 60 has been found to be more influential than the three aforementioned arcuate supporting surfaces 38, 40, 42. The third arcuate supporting surface 42 is then most influential, followed by the first arcuate supporting surface 38 and finally the second arcuate supporting surface 40.

If no blister crushing were to be incorporated into the inhaler 10, the device would still benefit from one or more of the three arcuate supporting surfaces 38, 40, 42 and/or the blister strip guide rib 60. However, the overall space required for the used and unused blister strip 12 when the combined diameter of the coiled used and unused blister strip 12 is at a maximum, would be higher.

With higher dose payload blisters, optimisation of the internal space required can still occur but again the peak sum diameter of the coiled used and unused blister strip 12 would be higher than it would be otherwise.

Optimisation would work for a 60 (sixty) dose inhaler 10 as well as a 30 (thirty) dose inhaler 10. With a 30 dose inhaler 10, the entire device could in theory be made proportionally smaller. However, in reality, since the cost of tooling has already been paid for once for the 60 dose configuration and a 30 dose inhaler 10 would use common components, it would be economically prudent to use the existing tooling. Furthermore, the question of optimising the internal space required for a 30 dose inhaler 10 would be rather moot simply because there would be plenty of space already available.

Many modifications and variations of the invention falling within the terms of the following claims will be apparent to those skilled in the art and the foregoing description should be regarded as a description of the preferred embodiments of the invention only. For example, although reference is made to a "mouthpiece", the invention is also applicable to devices in which the dose is inhaled through the nasal passages. Therefore, for the purposes of this specification, the term "mouthpiece" should also be construed so as to include within its scope a tube which is inserted into the nasal passages of a patient for inhalation therethrough.

Furthermore, although the blister piercing member is described as being attached to the mouthpiece so that the mouthpiece and the blister piercing member move together, it is also envisaged that the mouthpiece itself could remain stationary and the blister piercing element could be pivotally mounted to the mouthpiece so that the blister piercing member rotates relative to the mouthpiece to pierce the lid of an aligned blister.

In another embodiment, the cap and the actuating member could be combined into a single component so that rotation of the cap also causes indexing of the strip and piercing of an aligned blister.

It will be appreciated that the inhaler of the invention may be either a passive or active device. In a passive device, the dose is entrained in a flow of air caused when the user inhales through the mouthpiece. However, in an active device, the inhaler would include means for generating a pressurised flow of gas or air through the blister to entrain the dose and carry it out of the blister through the mouthpiece and into the user's airway. In one embodiment, the inhaler may be provided with a source of pressurised gas or air within the housing.

Reference is made throughout this specification to both "unused" and "used" blisters. It will be appreciated that "unused" blisters refer to those blisters that have not passed the blister piercing member and which remain intact with the dose contained therein. "Used" blisters refer to those blisters which have passed the blister piercing member in response to movement of the actuator by a user and which have been pierced to enable access to the dose contained therein to be obtained. Although in general, a "used" blister refers to a blister from which a dose has been inhaled, it should also be taken to include blisters which have passed the blister piercing member and have been pierced but which still contain either some or all of the dose contained therein. This may happen, for example, when a user moves the actuator to move the blister strip without inhaling the dose from a previously pierced blister.

The invention claimed is:

1. An inhaler, comprising
a housing,
a mouthpiece through which a dose of medicament is inhaled by a user,
a blister strip having a plurality of blisters, each blister containing, at least initially, a dose of medicament for inhalation by a user,
a blister opening assembly for facilitating withdrawal of medicament from a target blister of the blister strip,
an actuator mechanism operable to sequentially move each blister into alignment with the blister opening assembly so as to become said target blister,
the housing comprising a first blister compartment for storing an unopened portion of the blister strip as a first coil, a second blister compartment for receiving an opened portion of the blister strip and coiling it into a second coil, and a movable dividing wall separating the first and second blister compartments,
the movable dividing wall being displaced progressively during successive actuations of the inhaler, thereby causing the volume of the first blister compartment to decrease progressively and the volume of the second blister compartment to increase progressively, the inhaler further comprising
a first arcuate supporting surface which is disposed in, or forms part of, the first blister compartment within the housing for supporting at least a portion of the first coil,
wherein a radius of the first arcuate supporting surface matches the radius of the first coil, at a stage in the life of the inhaler, when the diameter of the first coil is at a maximum and
a blister strip guide rib for controlling the direction of the used blister strip as it enters the second blister compartment and for coiling the used blister strip back on itself so that a leading edge engages the used blister strip entering the second blister compartment to augment the movement of the blister strip forward, with a section of the used blister strip passing between the guide rib and an internal surface of the housing during successive actuations of the inhaler, wherein the blister strip has a height a when it is located in the second blister compartment and the guide rib is spaced apart from the internal surface of the housing by distance b to form a channel through which the section of the blister strip passes, wherein the section of the blister strip passing between the guide rib and the internal surface of the housing does not include a blister bowl which contained the dose of medicament before being opened,
characterized in-that the blister height a as the section of the blister strip passes through the channel is greater than the distance b of the channel.

2. The inhaler as claimed in claim 1, comprising a second arcuate supporting surface which is disposed in, or forms part of, the second blister compartment within the housing for supporting at least a portion of the second coil,
wherein a radius of the second arcuate supporting surface matches the radius of the second coil, at a stage in the life of the inhaler, when the diameter of the first coil is at or near a maximum.

3. The inhaler as claimed in claim 2, comprising a third arcuate supporting surface which is disposed in, or forms part of, the first blister compartment within the housing for supporting at least a portion of the first coil,
wherein a radius of the third arcuate supporting surface matches the radius of the first coil, at a stage in the life of the inhaler, when the sum diameter of the first and second coils is at a maximum.

4. The inhaler as claimed in claim 3, wherein the arcuate supporting surfaces extend from an internal surface of the housing.

5. The inhaler as claimed in claim 3, wherein the arcuate supporting surfaces extend from an internal wall disposed within the housing.

6. The inhaler as claimed in claim 3, wherein the first and/or third arcuate supporting surfaces have a length equivalent to an arc of the first coil of at least 30 degrees when the radius of the first coil is at a maximum.

7. The inhaler as claimed in claim 3, wherein the positions of the arcuate supporting surfaces relative to the housing are fixed such that they are immoveable.

8. The inhaler as claimed in claim 3, wherein the first coil is disposed intermediate the third arcuate supporting surface and the moveable dividing wall.

9. The inhaler as claimed in claim 2, wherein the second coil is disposed intermediate the second arcuate supporting surface and the moveable dividing wall.

10. The inhaler as claimed claim 1, further comprising a blister crushing member for at least partially squashing the blisters after they have been opened.

11. The inhaler as claimed in claim 3, wherein the second arcuate supporting surface has a length equivalent to an arc of the second coil of at least 30 degrees when the radius of the first coil is at a maximum.

12. The inhaler as claimed in claim 1, wherein the moveable dividing wall comprises an elongate foot which is attached to and integrally formed with a baffle.

13. The inhaler as claimed in claim 12, wherein the baffle has a linear body portion and an arcuate tail portion extending from a lower end of the linear body portion.

* * * * *